(12) United States Patent
Yuan et al.

(10) Patent No.: US 7,749,230 B2
(45) Date of Patent: *Jul. 6, 2010

(54) DEVICE AND METHOD FOR DISTRACTION OF THE SPINAL DISC SPACE

(75) Inventors: Philip S. Yuan, Fayetteville, NY (US); Kwan Ku Lin, Pasadena, CA (US); Robert M. Scribner, Niwot, CO (US)

(73) Assignee: Crosstrees Medical, Inc., Boulder, CO (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/574,562

(22) PCT Filed: Sep. 2, 2005

(86) PCT No.: PCT/US2005/031356
§ 371 (c)(1),
(2), (4) Date: Mar. 1, 2007

(87) PCT Pub. No.: WO2006/028986
PCT Pub. Date: Mar. 16, 2006

(65) Prior Publication Data
US 2008/0097511 A1 Apr. 24, 2008

Related U.S. Application Data

(60) Provisional application No. 60/606,611, filed on Sep. 2, 2004.

(51) Int. Cl.
*A61F 5/00* (2006.01)
*A61M 31/00* (2006.01)
(52) U.S. Cl. .................. 606/86 R; 604/60; 604/500

(58) Field of Classification Search ............. 604/57–64, 604/93.01, 500, 502; 606/92–94, 86; 623/17.12
See application file for complete search history.

(56) References Cited

U.S. PATENT DOCUMENTS 2,669,230 A 2/1954 Smoot (Continued)

FOREIGN PATENT DOCUMENTS

EP 1 495 729 A1 1/2005

(Continued)

OTHER PUBLICATIONS

International Search Report and Written Opinion for International Application PCT/US06/61207, mailed Oct. 5, 2007.

(Continued)

*Primary Examiner*—Kevin C Sirmons
*Assistant Examiner*—Catherine N Witczak

(57) ABSTRACT

An extractable device is used to insert a medicinal filling into a spinal disc. The device comprises a filling member and a flowable medicine. The filling member is made of a flexible and permeable wall and is provided with a holding portion and an injection port via which the flowable medicine is injected into the holding portion after the filling member is inserted into the spinal disc. The holding portion is provided with an opening which is releasably lashed by one end of one or more threads so as to make the opening leakproof. Upon completion of solidification of the flowable medicine in the holding portion of the filling member, other end of the thread is pulled to unlash the opening of the holding portion, thereby enabling the filling member to be extracted from the spinal disc so as to leave only the medicine in the spinal disc.

12 Claims, 7 Drawing Sheets

U.S. PATENT DOCUMENTS

| | | | |
|---|---|---|---|
| 4,188,949 A | 2/1980 | Antoshkiw | |
| 4,488,549 A | 12/1984 | Lee et al. | |
| 4,625,722 A | 12/1986 | Murray | |
| 4,969,888 A | 11/1990 | Scholten et al. | |
| 5,017,175 A | 5/1991 | Klusmire | |
| 5,054,492 A | 10/1991 | Scribner et al. | |
| 5,108,404 A | 4/1992 | Scholten et al. | |
| 5,549,679 A * | 8/1996 | Kuslich | 623/17.12 |
| 5,632,275 A | 5/1997 | Browne et al. | |
| 5,744,958 A | 4/1998 | Werne | |
| 5,782,764 A | 7/1998 | Werne | |
| 5,827,289 A | 10/1998 | Reiley et al. | |
| 5,972,015 A | 10/1999 | Scribner et al. | |
| 5,976,186 A | 11/1999 | Bao et al. | |
| 6,048,346 A | 4/2000 | Reiley et al. | |
| 6,053,904 A | 4/2000 | Scribner et al. | |
| 6,066,154 A | 5/2000 | Reiley et al. | |
| 6,146,422 A | 11/2000 | Lawson | |
| 6,235,043 B1 | 5/2001 | Reiley et al. | |
| 6,241,734 B1 | 6/2001 | Scribner et al. | |
| 6,245,107 B1 | 6/2001 | Ferree | |
| 6,248,110 B1 | 6/2001 | Reiley et al. | |
| 6,402,784 B1 | 6/2002 | Wardlaw | |
| 6,440,138 B1 | 8/2002 | Reiley et al. | |
| 6,443,988 B2 | 9/2002 | Felt et al. | |
| 6,468,279 B1 | 10/2002 | Reo | |
| 6,488,710 B2 | 12/2002 | Besselink | |
| 6,508,839 B1 | 1/2003 | Lambrecht et al. | |
| 6,533,817 B1 | 3/2003 | Norton et al. | |
| 6,558,390 B2 | 5/2003 | Cragg | |
| 6,575,919 B1 | 6/2003 | Reiley et al. | |
| 6,602,291 B1 | 8/2003 | Ray et al. | |
| 6,607,544 B1 | 8/2003 | Boucher et al. | |
| 6,632,235 B2 | 10/2003 | Weikel et al. | |
| 6,641,587 B2 | 11/2003 | Scribner et al. | |
| 6,645,213 B2 | 11/2003 | Scribner et al. | |
| 6,706,069 B2 | 3/2004 | Berger | |
| 6,712,819 B2 | 3/2004 | Zucherman et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,740,093 B2 * | 5/2004 | Hochschuler et al. | 606/94 |
| 6,923,813 B2 | 8/2005 | Phillips et al. | |
| 6,960,215 B2 | 11/2005 | Olson, Jr. et al. | |
| 6,979,341 B2 | 12/2005 | Scribner et al. | |
| 7,044,954 B2 | 5/2006 | Reiley et al. | |
| 7,081,122 B1 | 7/2006 | Reiley et al. | |
| 7,153,306 B2 | 12/2006 | Ralph et al. | |
| 7,166,121 B2 | 1/2007 | Reiley et al. | |
| 7,175,627 B2 | 2/2007 | Lin et al. | |
| 7,175,628 B2 | 2/2007 | Lin et al. | |
| 7,175,629 B2 | 2/2007 | Lin et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 7,465,318 B2 | 12/2008 | Sennett et al. | |
| 2002/0026195 A1 | 2/2002 | Layne et al. | |
| 2003/0036762 A1 | 2/2003 | Kerr et al. | |
| 2003/0050644 A1 | 3/2003 | Boucher et al. | |
| 2004/0059417 A1 * | 3/2004 | Smith et al. | 623/17.11 |
| 2004/0102774 A1 | 5/2004 | Trieu | |
| 2004/0106999 A1 | 6/2004 | Mathews | |
| 2004/0122455 A1 | 6/2004 | Lin | |
| 2004/0210297 A1 | 10/2004 | Lin et al. | |
| 2005/0065609 A1 | 3/2005 | Wardlaw | |
| 2005/0090852 A1 | 4/2005 | Layne et al. | |
| 2005/0228397 A1 | 10/2005 | Malandain et al. | |
| 2005/0267483 A1 | 12/2005 | Middleton | |
| 2006/0079905 A1 | 4/2006 | Beyar et al. | |
| 2006/0155296 A1 | 7/2006 | Richter | |
| 2006/0229625 A1 | 10/2006 | Truckai et al. | |
| 2006/0247648 A1 | 11/2006 | Serbousek | |
| 2007/0129669 A1 | 6/2007 | Lin et al. | |
| 2007/0129670 A1 | 6/2007 | Lin et al. | |
| 2007/0142765 A1 | 6/2007 | Lin et al. | |
| 2007/0156242 A1 | 7/2007 | Lin et al. | |
| 2009/0254132 A1 | 10/2009 | Scribner et al. | |

FOREIGN PATENT DOCUMENTS

| | | |
|---|---|---|
| EP | 1 495 730 A1 | 1/2005 |
| EP | 1 588 674 | 10/2005 |
| EP | 1 588 732 | 10/2005 |
| EP | 1 882 459 | 1/2008 |
| WO | WO 2002/026170 A2 | 4/2002 |
| WO | WO 03/057088 A1 | 7/2003 |
| WO | WO 2009/036466 | 3/2009 |

OTHER PUBLICATIONS

European Office Action for EP 05794205.4, mailed Oct. 2, 2009.
Chinese Office Action for 200680043269.1, mailed Sep. 25, 2009.
International Search Report for PCT/US2005/031356, mailed Apr. 7, 2006.
Office Action for U.S. Appl. No. 11/674,085, mailed Nov. 4, 2009.
Office Action for U.S. Appl. No. 11/674,085, mailed Apr. 3, 2009.
Office Action for U.S. Appl. No. 11/674,085, mailed Apr. 22, 2008.
Office Action for U.S. Appl. No. 11/674,085, mailed Nov. 29, 2007.
Office Action for U.S. Appl. No. 11/674,085, mailed Jun. 11, 2007.
Office Action for U.S. Appl. No. 11/674,088, mailed Jun. 8, 2007.
Office Action for U.S. Appl. No. 11/674,088, mailed Nov. 28, 2007.
Office Action for U.S. Appl. No. 11/674,088, mailed Apr. 22, 2008.
Office Action for U.S. Appl. No. 11/674,088, mailed Oct. 24, 2008.
Office Action for U.S. Appl. No. 11/674,088, mailed Jul. 9, 2009.

* cited by examiner

DEVICE AND METHOD FOR DISTRACTION OF THE SPINAL DISC SPACE

CROSS-REFERENCE TO RELATED APPLICATIONS

This application claims priority from International Application No. PCT/US05/31356, filed Sep. 2, 2005, which claims priority from U.S. Provisional Application No. 60/606,611, filed Sep. 2, 2004.

FIELD OF THE INVENTION

The present invention relates generally to an instrument which is used in the restorative surgical treatment of spine disorder. More specifically this surgical instrument can be used to insert a medical material into a spinal disc such that the instrument can be separated from the medical material and drawn out of the spinal disc, and the medical material remains in the spinal disc in a restorative function.

BACKGROUND OF THE INVENTION

The surgical treatment of spinal disc disorder can be generally attained by several methods, which include the hypodermic injection of medicine, the balloon-insertion of medicine, and the filler-insertion of medicine. For example, the U.S. Pat. Nos. 5,976,186, 6,508,839, and 6,602,291 disclose respectively methods for treating disorders of the spinal disc, such as placement of a prosthetic device or reconstruction of the damaged structure of the disc. These methods are defective in design in that disc disruption is required for placement of the therapeutic implant. The placement of a therapeutic implant by controlled delivery of a flowable material requiring minimal disruption of the disc is desirable. Without controlled delivery, the medicine is not contained and there is the possibility of injury to the surrounding tissues.

In order to prevent the drawbacks of the methods described above, the filler-insertion method is used to implant material in the spinal disc in such a way that the material is contained in the spinal disc, and that the material only remains implanted in the spinal disc.

SUMMARY OF THE INVENTION

An extractable device for inserting a medicinal filling into a spinal disc, said device comprising:

a filling member comprising a flexible wall and provided with a holding portion, an injection port at one end of the holding portion, and an opening at another end of the holding portion;

one or more thread, each having one end for fastening releasably said opening of said holding portion in such a manner that said opening is leakproof; and a flowable medicine to be injected into said holding portion via said injection port of said filling member in the wake of a process for inserting said filling member into the spinal disc whereby said flowable medicine solidifies in said holding portion of said filling member;

said opening of said holding portion being unfastened at the time when other end of said threads is pulled by an external force, thereby enabling said filling member to be extracted from the spinal disc so as to leave only said flowable material in the spinal disc;

wherein the volume of said holding portion of said filling member is filled and is substantially tubular after being filled, wherein cross sections perpendicular to a longitudinal axis of the holding portion are substantially elliptical along a direction from the injection port to the opening of the holding portion.

Preferably, said flexible wall is provided with a plurality of through holes and is permeable. Said flexible and permeable wall is of a one-layered or multi-layered construction.

Preferably, said flowable medicine is a polymer substance such as a mixture which is flowable prior to setting to a non-viscous state such as PMMA, silicone, polyurethane, polyester, or other polymer.

Preferably, the device of the present invention further comprises an injection tool for injecting said flowable medicine into said holding portion via said injection port.

Preferably, said injection tool comprises a guide tube and a syringe, wherein one end of said guide tube is connected to said injection port of said filling member and another end of said guide tube is connected to said syringe in which said flowable medicine is held, so that said flowable medicine is able to be injected into said holding portion of said filling member by said syringe via said injection port and said guide tube.

Preferably, the device of the present invention further comprises a working tube for inserting into said spinal disc, so that said filling member together with said guide tube can be inserted into said working tube and said filling member can be disposed in said spinal disc.

Preferably, said tubular wall is provided with a plurality of through holes and is permeable.

The present invention also discloses a method for implanting a solidified medicine into a spinal disc comprising:

inserting a filling member in a hole of a spinal disc, said filling member comprising a flexible and permeable wall and provided with a holding portion, an injection port at one end of the holding portion, and an opening at another end of the holding portion, wherein one or more thread is provided and each having one end fastening releasably said opening of said holding portion in such a manner that said opening is leakproof, wherein said holding portion of said filling member is substantially tubular after being filled, wherein cross sections perpendicular to a longitudinal axis of the holding portion are substantially elliptical along a direction from the injection port to the opening of the holding portion;

injecting a flowable medicine into said holding portion via said injection port of said filling member, so that said holding portion is inflated and said flowable medicine solidifies in said holding portion of said filling member; and unfastening said opening of said holding portion by pulling other end of said threads, thereby enabling said filling member to be extracted from the spinal disc so as to leave only said solidified medicine in the spinal disc, wherein said solidified flowable medicine has a shape similar to that of the inflated holding portion.

Preferably, the method of the present invention further comprises fastening detachably an injection tool with said filling member, so that said flowable medicine is injected into said holding portion via said injection tool. More preferably, said injection tool comprises a guide tube and a syringe, wherein one end of said guide tube is connected to said injection port of said filling member and another end of said guide tube is connected to said syringe in which said flowable medicine is held, wherein said flowable medicine is injected into said holding portion of said filling member by said syringe via said injection port and said guide tube.

Preferably, the method of the present invention further comprises inserting a working tube in said hole of said spinal disc, and inserting said filling member together with said guide tube into said working tube, so that said filling member is disposed in said spinal disc.

The flexible wall of the filling member of the present invention is made of a biocompatible or biosynthetic material, such as polymer, rubber, elastic plastic, PTFE, Dacron, and like materials. The flexible wall is provided with a plurality of pores and is therefore permeable. Pores may be provided by fabricating the wall from a weave of selected material, or by perforation of a film of selected material. The flexible wall can be formed into an object in the form of sac, bag, ball, cylinder or rectangular column integrally or by joining separate pieces.

The filling member of the present invention may contain a radiopaque material, such as a metal wire, by which the precise position of the filling member can be easily located by an imaging system, such as X-ray imaging equipment.

The flexible wall of the filling member of the present invention may be of a one-layered or multi-layered construction, depending on the particle size and the viscosity of the medicine. If the particle size of the medicine is relatively large, the flexible wall is preferably of a two-layered construction. If the viscosity of the medicine is relatively high, the flexible wall is also preferably of a two-layered construction. On the other hand, the flexible wall is preferably of a three-layered or four-layered construction under the circumstances that the particle size of the medicine is relatively small and that the viscosity of the medicine is relatively lower.

The features and the advantages of the present invention will be more readily understood upon a thoughtful deliberation of the following detailed description of the preferred embodiments of the present invention with reference to the accompanying drawings.

DETAILED DESCRIPTION OF THE PREFERRED EMBODIMENTS

Figure 1:
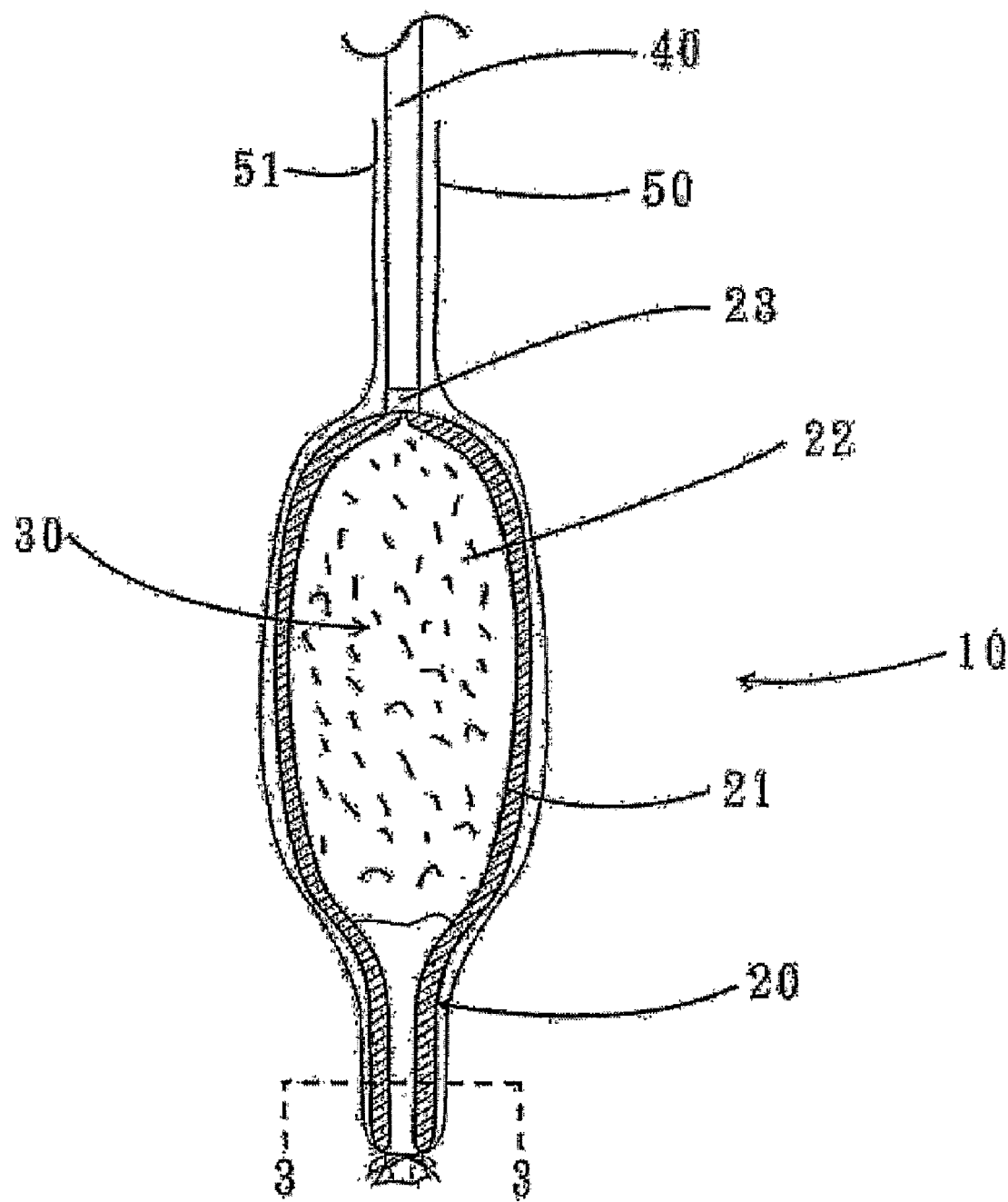
FIG. 1 shows a schematic view of an extractable filler of the present invention.

As shown in FIG. 1, an extractable filler 10 embodied in the present invention comprises a filling member 20, a flowable medicine 30, a guide tube 40, and two threads 50 and 51. The filling member 20 is formed of a flexible wall 21 and is provided with a holding portion 22 and an injection port 23. The flexible wall 21 may be made of rubber or a flexible plastic material with perforated holes, or a woven fabric. The flowable medicine 30 is injected into the holding portion 22 via the guide tube 40 and the injection port 23. The dotted line 3-3 shows a direction in which a section of the filling member 20 is taken.

Figure 2:
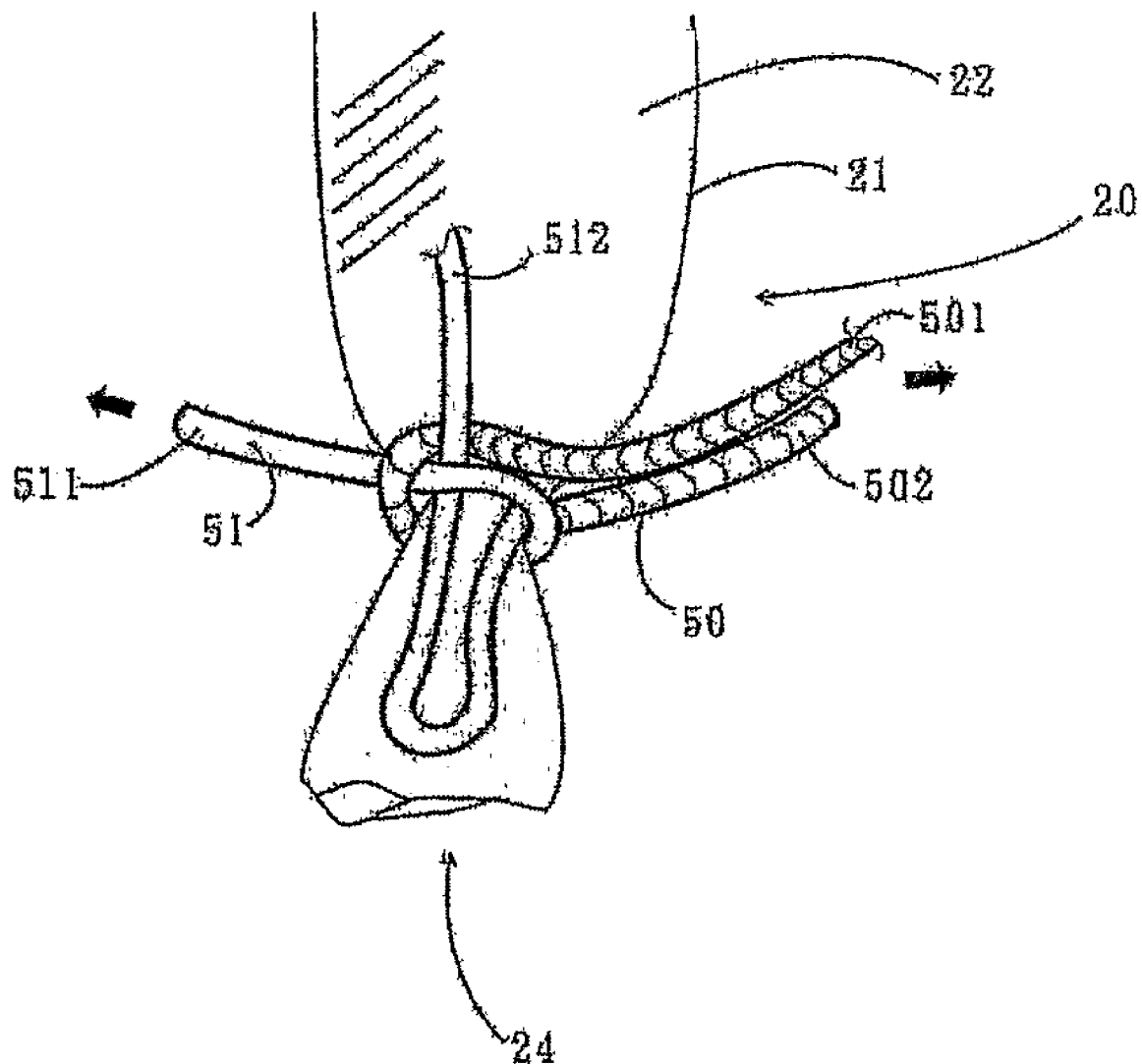
FIG. 2 is schematic view illustrating the lashing of the opening of the holding portion of the filling member of the present invention.

As shown in FIG. 2, the holding portion 22 of the filling member 20 is provided with an opening 24 opposite to the injection port 23 of the filling member 40. The opening 24 is lashed by two threads 50 and 51. The first thread 50 has a first end 501 and a second end 502, while the second thread 51 has a first end 511 and a second end 512. The two threads 50 and 51 are in fact fastened releasably to the flexible wall 21 near the opening 24. The way by which they are fastened together is not shown in the drawing.

Figure 5A:
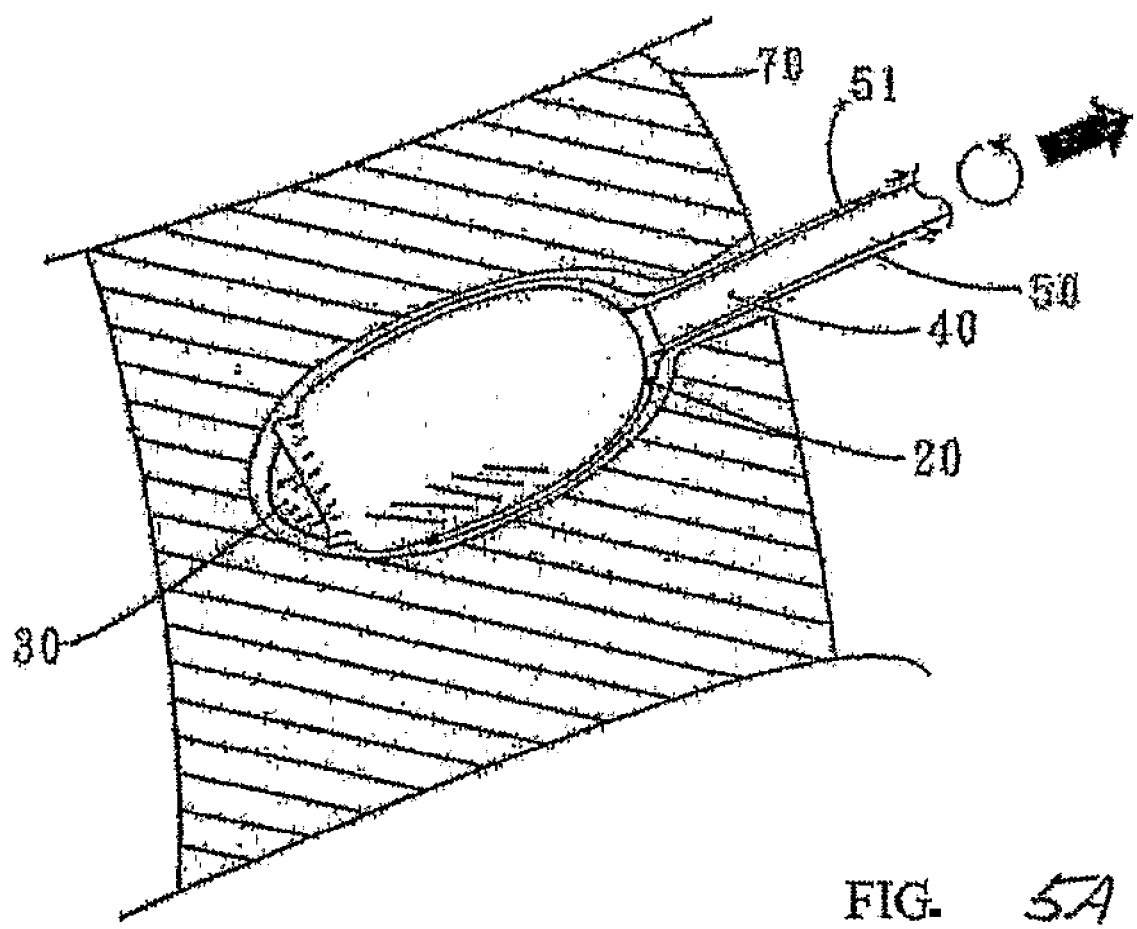
FIG. 5a shows a sectional view of the filling member with the said opening in the open condition.

The opening 24 of the holding portion 22 of the filling member 20 is securely tied up to prevent the medicine 30 from leaking out of the holding portion 22 by means of the two threads 50 and 51 which are releasably entangled in such a manner that the first end 511 of the second thread 51 is wound around the first thread 50. Upon completion of the winding process, the flexible wall 21 surrounding the opening 24 is located in a position between the two threads 50 and 51. Thereafter, both ends 501 and 502 of the first thread 50, and the first end 511 of the second thread 51 are respectively pulled rightward and leftwards at the same time, as illustrated in FIG. 2. As a result, the opening 24 of the filling member 20 is leakproof. The opening 24 of the filling member 20 is untied when the second end 512 of the second thread 51 is pulled in the direction of the injection port 23. As a result, the two threads 50 and 51 become loosened. Thereafter, the first end 501 of the first thread 50 and the second end 512 of the second thread 51 are respectively pulled in a direction away from the opening 24 of the filling member 20, as illustrated in FIG. 5a. The opening 24 is thus unfastened completely.

Figure 3A:
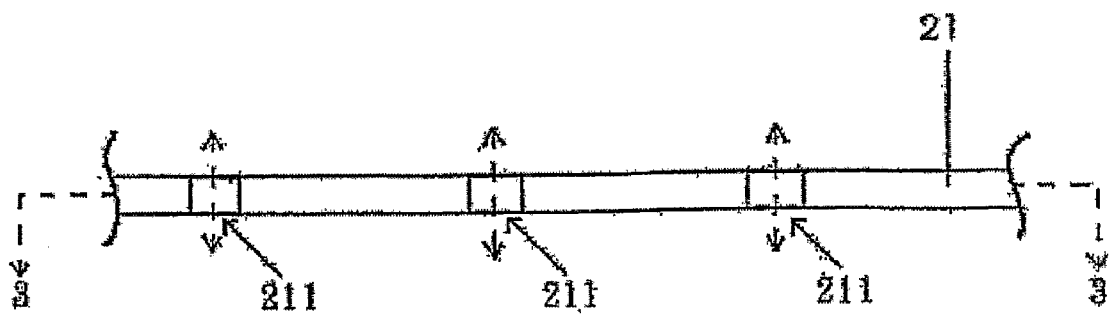
FIG. 3a shows a longitudinal sectional view of a one-layered wall of the filling member of the present invention.
Figure 3B:
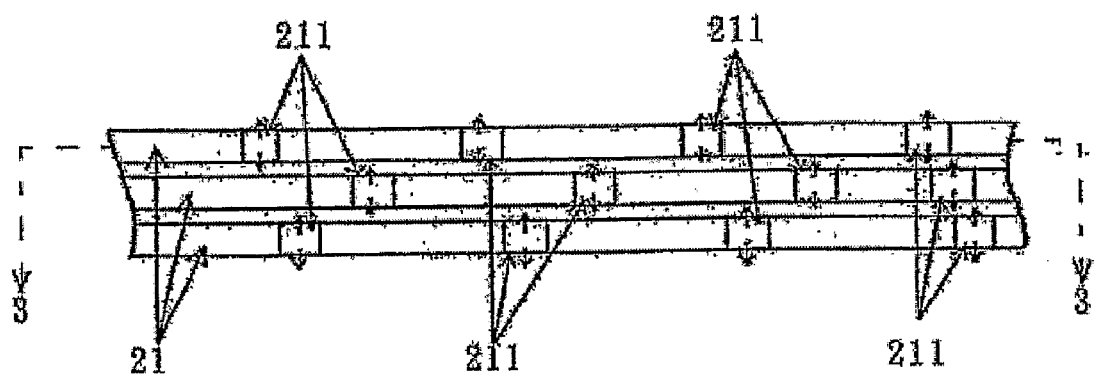
FIG. 3b shows a longitudinal sectional view of a multi-layered wall of the filling member of the present invention.

The flexible wall 21 of the filling member 20 is of a one-layered construction, as shown in FIG. 3a, or of a multi-layered construction, as shown in FIG. 3b. The flexible wall 21 is provided with a plurality of pores 211 permeable to fluids. If the flexible wall 21 is of a multi-layered construction, the flexible walls 21 are laminated in such a way that the pores 211 are not corresponding in location to slow down the passage of the fluids.

Figure 4A:
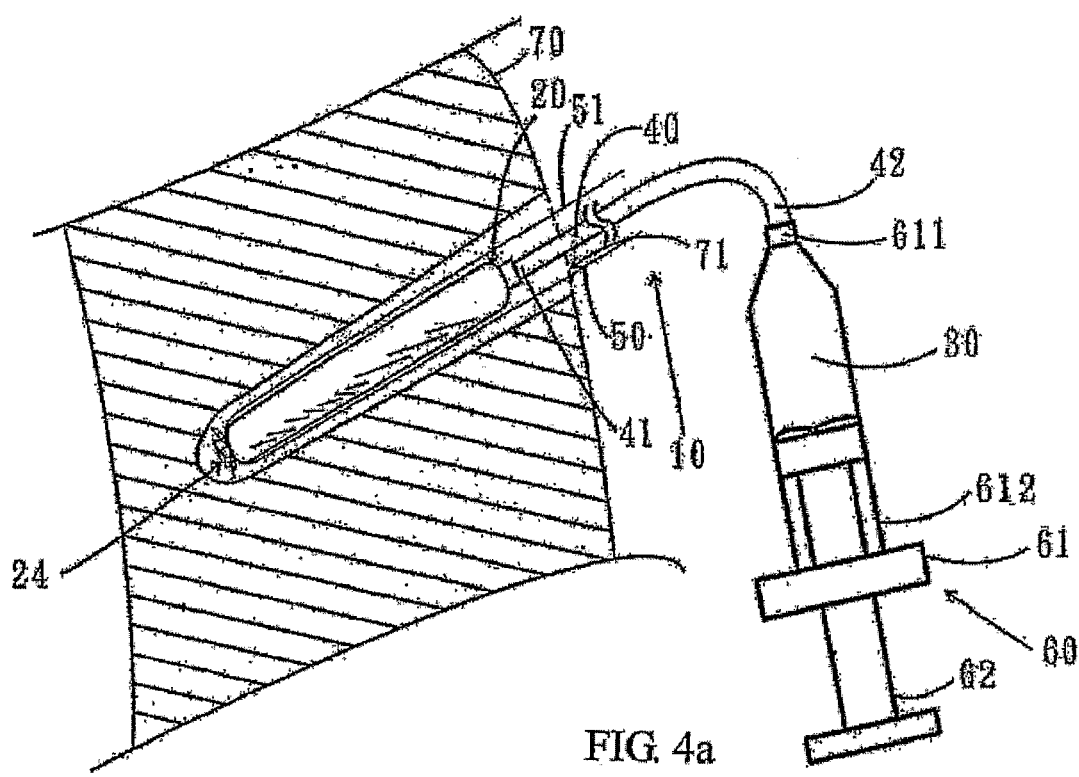
FIG. 4a shows a sectional view of the filling member placed within the spinal disc.
Figure 4B:
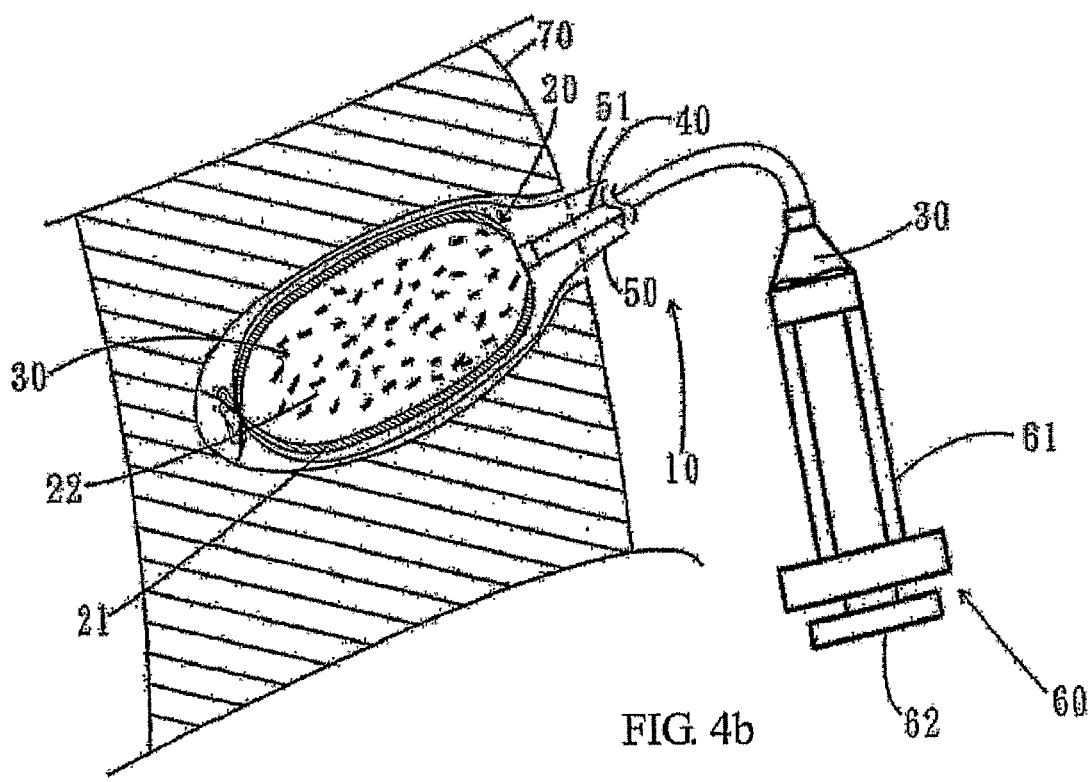
FIG. 4b shows a sectional view of the filling member placed within the spinal disc containing a full volume of flowable material.

As shown in FIG. 4a, the filling member 20 of the extractable filler 10 is inserted into a hole 71 formed on a spinal disc 70, wherein a working tube 51 is inserted into the hole 71 in advance to accommodate the guide tube 40, the threads 50 and 51 and the filling member 20. The flowable medicine is then injected into the holding portion 21 of the filling member 20 by a syringe in conjunction with the guide tube 40. The guide tube 40 has one end 41 in the holding portion 21, and another end 42 connected to one end 611 of a barrel 612 of the syringe 80. A plunger 62 is inserted into another end of the barrel 612 in which the pasty medicine 30 is contained. The filling member 20 is thus inflated by the medicine 30, as shown in FIGS. 4a and 4b.

Preferably, said flowable medicine 30 is a polymer substance such as a mixture which is flowable prior to setting to a non-viscous state such as PMMA, silicone, polyurethane, polyester, or other polymer.

Upon completion of the solidification of the pasty medicine 30 in the filling member 20 within the spinal disc 70, the filling member 20 must be extracted from the hole 71 of the spinal disc 70, so as to leave only the medicine 30 in the spinal disc 70. The extraction of the filling member 20 from the hole 71 of the spinal disc 70 involves a first step in which the second end 512 of the second thread 51 is pulled in the direction of the filler opening 23. As a result, the two threads 50 and 51 become loosened. Thereafter, the first end 501 of the first thread 50 and the second end 512 of the second thread 51 are respectively pulled in a direction away from the opening 24 of the filling member 20, as illustrated in FIG. 5a. The opening 24 is thus unfastened completely.

Figure 5B:
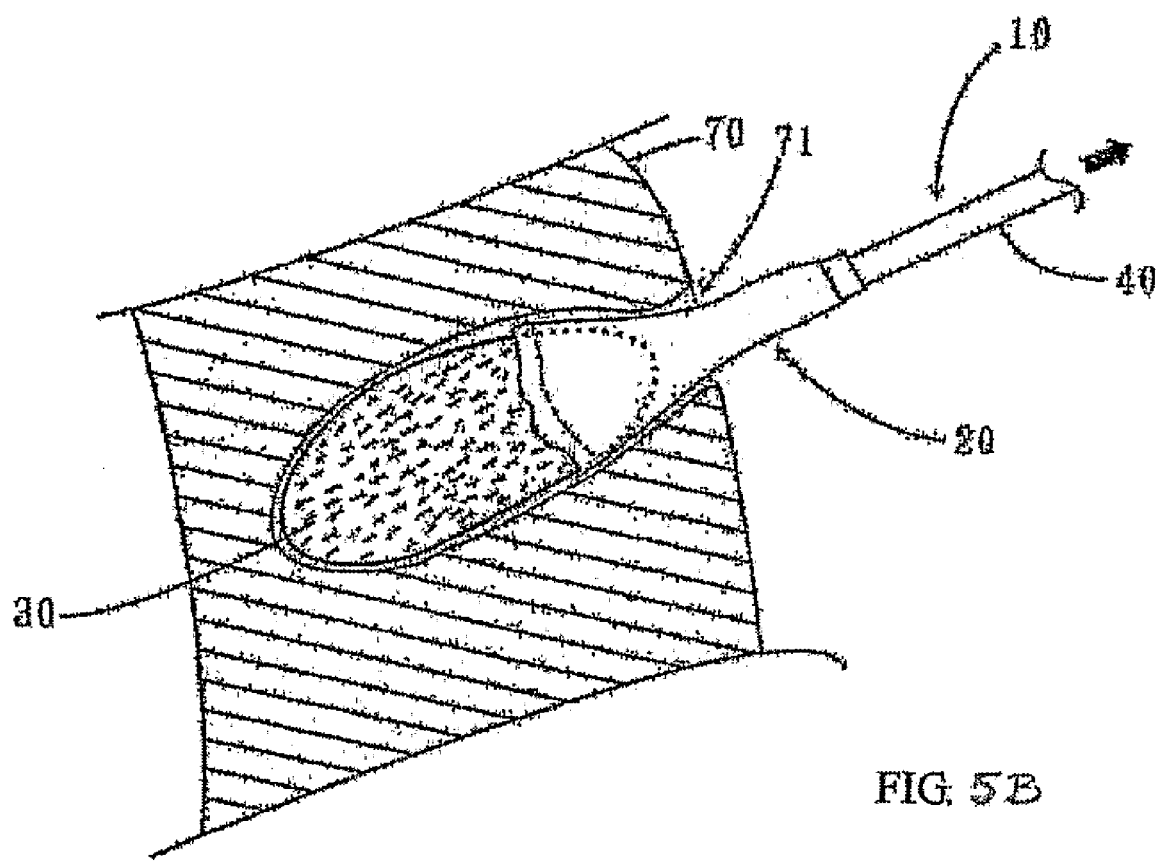
FIG. 5b is a sectional view showing the removal of the filling member from the spinal disc.

After the opening 24 being unfastened, the flexible wall 21 is retreated from the solidified medicine 30 by pulling one end of the flexible wall 21 connected to the guide tube 40 at the injection port 23 of said holding portion of the said filling member 20, whereby said solidified medicine 30 is released from said filling member 20 and is disposed in the spinal disc 70, as shown in FIG. 5b. The filling member and the guide tube 40 are pulled from the hole 71 of the spinal disc 70, so as to leave only said solidified medicine 30 in the spinal disc 70.

Figure 6A:
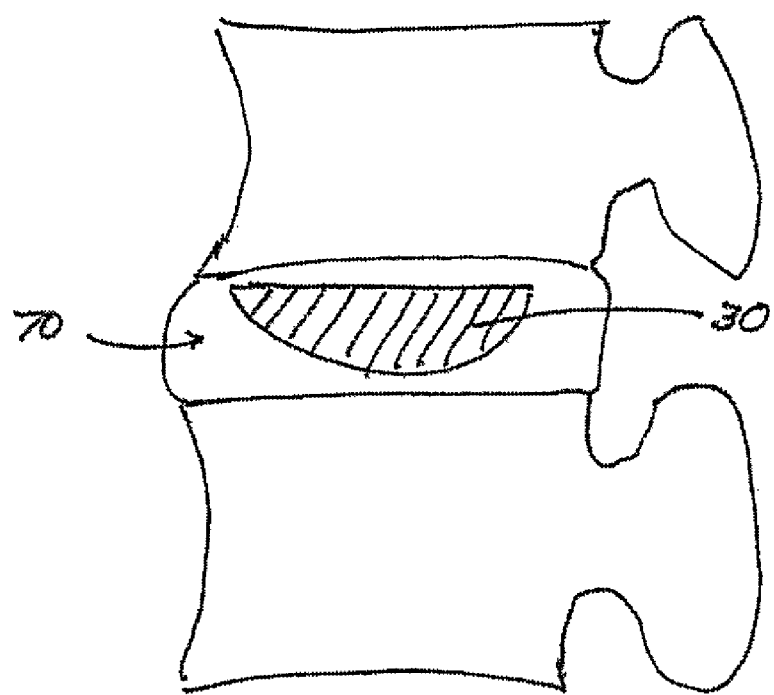
FIG. 6a is a sectional view showing the flowable material within the spinal disc.

The flexible wall 21 of the filling member 20 of the extractable filler 10 of the present invention may have a curved profile. As shown in FIG. 6a, the flowable material 30 injected into the filling member 20 in the spinal disc 70 will also have a curved profile when remaining within the spinal disc 70.

Figure 6B:
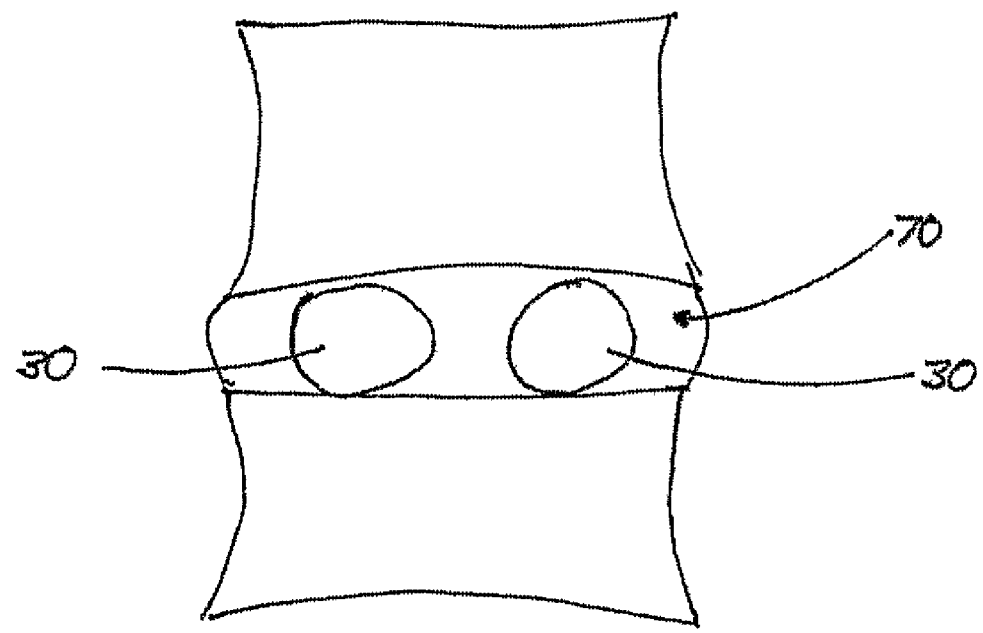
FIG. 6b is a sectional view showing the flowable material at more than one location within the spinal disc.

As shown in FIG. 6b, the filling member 20 may be placed at more than one location in the spinal disc, with the flowable material 30 remaining at more than one location in the spinal disc 70.

The above embodiments are, in all respects, illustrative and nonrestrictive. The invention may be embodied in other specific forms without deviating from the scope of the following claims.

What is claimed is:

1. An extractable device for inserting a medicinal filling into a spinal disc, said device comprising: a filling member comprising a flexible wall and provided with a holding portion, an injection port at one end of the holding portion, and a previously created releasably closable opening at a distal end of the holding portion; one or more thread fastening releasably said opening of said holding portion in such a manner that said opening is leakproof; and a flowable medicine to be injected into said holding portion via said injection port of said filling member in the wake of a process for inserting said filling member into the spinal disc; said opening of said holding portion being reopened without permanently severing the filling member, thereby enabling said filling member to be extracted from the spinal disc so as to leave only said medicine in the spinal disc.

2. The device as defined in claim 1, wherein said flexible wall is provided with a plurality of through holes and is permeable.

3. The device as defined in claim 2, wherein said flexible and permeable wall is of a one-layered or multi-layered construction.

4. The device as defined in claim 1, wherein said flowable material is a polymer capable of setting to a non-viscous state.

5. The device as defined in claim 1 further comprising an injection tool for injecting said flowable medicine into said holding portion via said injection port.

6. The device as defined in claim 5, wherein said injection tool comprises a guide tube and a syringe, wherein one end of said guide tube is connected to said injection port of said filling member and another end of said guide tube is connected to said syringe in which said flowable medicine is held, so that said flowable medicine is able to be injected into said holding portion of said filling member by said syringe via said injection port and said guide tube.

7. The device as defined in claim 6 further comprising a working tube for inserting into said spinal disc, so that said filling member together with said guide tube can be inserted into said working tube and said filling member can be disposed in said spinal disc.

8. A method for implanting a solidified medicine into a spinal disc comprising: inserting a filling member in a hole of a spinal disc, said filling member comprising a flexible and permeable wall and provided with a holding portion, an injection port at one end of the holding portion, and a previously created releasably closable opening at a distal end of the holding portion, wherein one or more thread is provided and each having one end fastening releasably said opening of said holding portion in such a manner that said opening is leakproof, wherein said holding portion of said filling member is inflatable; injecting a flowable medicine into said holding portion via said injection port of said filling member, so that said holding portion is inflated and said flowable medicine solidifies in said holding portion of said filling member; and pulling other end of said threads, thereby reopening without permanently severing the filling member and enabling said filling member to be extracted from the spinal disc so as to leave only said solidified medicine in the spinal disc, wherein said solidified flowable medicine has a shape similar to that of the inflated holding portion.

9. The method as defined in claim 8, wherein said flowable material is a polymer capable of setting to a non-viscous state.

10. The method as defined in claim 8 further comprising fastening detachably an injection tool with said filling member, so that said flowable medicine is injected into said holding portion via said injection tool.

11. The method as defined in claim 10, wherein said injection tool comprises a guide tube and a syringe, wherein one end of said guide tube is connected to said injection port of said filling member and another end of said guide tube is connected to said syringe in which said flowable medicine is held, wherein said flowable medicine is injected into said holding portion of said filling member by said syringe via said injection port and said guide tube.

12. The method as defined in claim 11 further comprising inserting a working tube in said hole of said spinal disc, and inserting said filling member together with said guide tube into said working tube, so that said filling member is disposed in said spinal disc.

* * * * *